(12) United States Patent
Devisetty et al.

(10) Patent No.: US 10,238,103 B2
(45) Date of Patent: Mar. 26, 2019

(54) RHIZOBIA AND MYCORRHIZAL GRANULAR FORMULATIONS AND MIXTURES THEREOF

(71) Applicant: Valent BioSciences LLC, Libertyville, IL (US)

(72) Inventors: Bala N. Devisetty, Buffalo Grove, IL (US); Mayur K. Soni, Hoffman Estates, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

(21) Appl. No.: 16/056,637

(22) Filed: Aug. 7, 2018

(65) Prior Publication Data
US 2019/0045779 A1    Feb. 14, 2019

Related U.S. Application Data

(60) Provisional application No. 62/542,363, filed on Aug. 8, 2017.

(51) Int. Cl.
*A01N 25/12* (2006.01)
*A01N 63/04* (2006.01)
*A01N 63/00* (2006.01)

(52) U.S. Cl.
CPC ............. *A01N 25/12* (2013.01); *A01N 63/00* (2013.01); *A01N 63/04* (2013.01)

(58) Field of Classification Search
None
See application file for complete search history.

(56) References Cited

U.S. PATENT DOCUMENTS 8,846,569 B2 *   9/2014   Meng .................... A01N 37/36
                                                    504/100
9,487,749 B2 *   11/2016  Benjamin ............. A61K 31/10

* cited by examiner

*Primary Examiner* — Alton N Pryor
(74) *Attorney, Agent, or Firm* — Wood, Phillips, Katz, Clark & Mortimer

(57) ABSTRACT

The present invention is directed to *Rhizobia* and Mycorrhizae granular formulations and methods of their use. The present invention is further directed to homogenous mixtures of *Rhizobia* granules and Mycorrhizae granules and methods of their use. The present invention is further directed to a process for preparing a homogenous mixture of *Rhizobia* granules and Mycorrhizae granules.

15 Claims, No Drawings

RHIZOBIA AND MYCORRHIZAL GRANULAR FORMULATIONS AND MIXTURES THEREOF

FIELD OF THE INVENTION

The present invention relates to *Rhizobia* and Mycorrhizae granular formulations and methods of their use. The present invention further relates to homogenous mixtures of *Rhizobia* granules and Mycorrhizae granules and methods of their use. The present invention further relates to a process for preparing a homogenous mixture of *Rhizobia* granules and Mycorrhizae granules.

BACKGROUND OF THE INVENTION

Huge amounts of water and fertilizer are utilized across agricultural and landscaping practices. These practices, although readily accepted and necessary, lead to an exacerbation of water quantity and quality issues across the world. For example, agriculture uses about 70% of accessible freshwater. Water that is not used may be contaminated by toxic chemicals found in pesticides and fertilizers. Specifically, contamination of municipal water supplies by nitrates is harmful to human health and increased phosphate content in rivers and streams leads to lower oxygen levels limiting survival of fish and other aquatic life.

*Rhizobia* are bacteria capable of forming a symbiotic association with the roots of plants. *Rhizobia* benefit the host plant by fixing atmospheric nitrogen into a more readily available form to the host plant. This fixing of atmospheric nitrogen is especially important for areas where crops are grown and harvested year after year as the nitrogen naturally found in the soil is systematically depleted or limited. *Rhizobia* thus reduce the need for nitrogen fertilizers to be applied to new crop plantings after the previous crop has been harvested. *Rhizobia* have further been shown to increase plant growth and yield.

Mycorrhizal fungi form symbiotic associations with the roots of plants. Mycorrhizal fungi are known to be associated with greater than 90% of all land plants including crops, grasses and trees. Mycorrhizal fungi provide many important benefits to plants including enhanced absorption of water and nutrients from the soil, increased drought tolerance, increased pathogen resistance and protection, enhanced plant health and vigor, minimized effects of external stress, and enhanced seedling growth. In turn, the external application of Mycorrhizal fungi to plants can lead to less irrigation and fertilization, which conserves water and reduces the amount of chemicals, such as nitrates and phosphorus, and essential micronutrients. Mycorrhizal fungi are most effective when introduced to the soil prior to seed germination or at early stages of plant root proliferation.

Currently, *Rhizobia* is most readily available as an aqueous inoculant in sterile pouches that must be stored cold at 5° C. Prior to application to the field, the *Rhizobia* inoculant is conveniently formulated on to peat granules while being blended in a blending equipment such as a Munson mixer, a Marion mixer or any other suitable mixing equipment. Blending of the granules may result in attrition leading to loss of integrity. This application process has proved somewhat successful; however, the cost of granules is high and the granules have an in-consistent nature. Further, due to the difference in formulation types and granule types used to apply *Rhizobia* and Mycorrhizae these two beneficial products are often applied inconsistently leading to less than ideal results.

Biodac® (Biodac is a registered trademark of Kadent Gran Tek Inc.) is a 100% biodegradable granule. Further, Biodac® is low cost, readily available, resistant to attrition due to mixing and has a neutral pH. Biodac® is available in several size grades from $4/10$ mesh down to $20/50$ mesh all of which are classified as an exempt inert material by the U.S. Environmental Protection Agency. However, to date, only pesticides have been successfully combined with Biodac® granules.

Accordingly, there is a need in the art for *Rhizobia* granular formulations that are stable and available. Further, there is a need in the art for stable and homogenous mixtures of Mycorrhizae granules and *Rhizobia* granules.

SUMMARY OF THE INVENTION

The present invention is directed to *Rhizobia* granular formulations comprising:
  from about 20% to about 31% w/w *Rhizobia* inoculant;
  from about 0.5% to about 3.0% w/w polyethylene glycol;
  from about 0.05% to about 0.5% w/w polysorb ate;
  from about 0.3% to about 1.0% w/w silicon dioxide powder; and
  from about 64% to about 74% w/w of a granule.

The present invention is further directed to Mycorrhizae granular formulations comprising:
  from about 0.01% to about 0.5% w/w Mycorrhizae concentrate;
  from about 10% to about 20% w/w soybean oil;
  from about 0.1% to about 0.5% w/w lecithin;
  from about 0.05% to about 0.5% w/w silicon dioxide powder; and
  from about 78% to about 85% w/w of a granule.

In a preferred composition, the granule comprises from about 47% to about 53% w/w paper fiber, from about 28% to about 34% w/w kaolin clay, from about 14% to about 20% w/w calcium carbonate and titanium oxide.

The present invention is further directed to granular mixtures comprising *Rhizobia* granule formulations of the present invention and Mycorrhizae formulations of the present invention.

The present invention is further directed to a process for preparing granular mixtures of *Rhizobia* granule formulations of the present invention and Mycorrhizae formulations of the present invention comprising:
  adding 1 part of the *Rhizobia* granule formulation of the present invention to a V-cone blender;
  adding 2 parts of the Mycorrhizae granule formulation of the present invention to the V-cone blender;
  adding 1 part of the *Rhizobia* granule formulation of the present invention to the V-cone blender; and
  blending in the V-cone blender for 5 to 20 minutes.

The present invention is further directed to methods of enhancing plant growth comprising applying a formulation or mixture of the present invention to the plant, plant propagation material thereof or to any area where the plant will grow.

DETAILED DESCRIPTION OF THE INVENTION

*Rhizobium* granules may contain up to 30 to 35% moisture thus limiting mixture formulation with Mycorrhizae, which under such high moisture environment have the potential to germinate and lose viability. There is currently no commercial granular formulation that mixes both *Rhizobium* and Mycorrhizae. However, having both *Rhizobium* and Mycorrhizae granules in the same package would be advantageous as both beneficial microbes will be evenly distributed in the root zone. Combining each granular formulation in the seed hopper does not result in homogenous application. In addition, these are not formulated onto the same type and size of granular carriers. The present invention relates to a novel method of combining both *Rhizobium* and Mycorrhizae granules formulated with the same type of carrier with similar physical and chemical properties. In order to prevent Mycorrhizae germination and loss of viability, the Mycorrhizae are formulated in a non-aqueous liquid prior to formulating onto a granular carrier thus protecting Mycorrhizae.

According to the present invention that *Rhizobia* and Mycorrhizae can be formulated such that each can be absorbed or adhered to the same type of carrier granule to promote homogenous mixing and application. This homogenous mixing and application provides an advantage over the prior art separate applications as it ensures that both the *Rhizobia* and Mycorrhizae are applied to every plant at the proper rate.

As used herein, the terms "Mycorrhiza" or "Mycorrhizae" refers to an organic material containing a Mycorrhizal fungus and the plant material to which the Mycorrhizal fungus is symbiotically associated. The symbiotic association of the Mycorrhizal fungus to the plant material may be either intracellular (i.e. arbuscular Mycorrhiza) or extracellular (i.e. ectomycorrhiza). Other types of Mycorrhiza, such as ericoid, arbutoid, monotropoid and Orchid Mycorrhiza, are also encompassed within the term "Mycorrhiza" or "Mycorrhizae."

As used herein, the terms "*Rhizobium*" or "*Rhizobia*" refers to bacteria that fix nitrogen after becoming established inside root nodules of plants.

As used herein, the term "propagules" refers to any material capable of propagating an organism, such as seeds, spores, roots, cuttings, cut shoots and the like.

As used herein, the term "plant propagation material" refers to seeds of all kinds (fruit, tubers, grains), roots, cuttings, cut shoots and the like.

As used herein % w/w denotes weight by total weight of the composition. All concentrations listed herein are in % w/w unless otherwise described.

The articles "a," "an" and "the" are intended to include the plural as well as the singular, unless the context clearly indicates otherwise.

As used herein, all numerical values relating to amounts, ratios, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

A U.S. Mesh size of 12 has sieve openings of 1680 microns in diameter and a U.S. Mesh size of 20 has sieve openings of 841 microns in diameter. A substance described as 12/20 Mesh would readily pass through a 12-mesh but not a 20-mesh sieve.

As used herein, "enhancing" means that the plant has more of the specific quality than the plant would have had if it had not been treated by methods of the present invention.

Polyethylene glycols are compounds containing a repeating subunit of the following molecular structure H—(O—$CH_2$—$CH_2)_n$—OH. Polyethylene glycols are identified based on their average molecular weight. For example, a polyethylene glycol with an average molecular weight of 400 daltons is named polyethylene glycol 400. In a preferred embodiment, the polyethylene glycol has an average molecular weight from about 100 to about 400 daltons, more preferably the polyethylene glycol is polyethylene glycol 200.

Polysorbates are ethoxylated sorbitans esterified with fatty acids. Common polysorbates include polyoxyethylene (20) sorbitan monolaurate ("polysorbate 20"), polyoxyethylene (20) sorbitan monopalmitate ("polysorbate 40"), polyoxyethylene (20) sorbitan monostearate ("polysorbate 60") and polyoxyethylene (20) sorbitan monooleate ("polysorbate 80"). Polysorbates are sold under the trademark Tween® (Tween is a registered trademark of Croda Inc.), including Tween® 20, 40, 60, or 80.

In one embodiment, the present invention is directed to *Rhizobia* granular formulations comprising:
from about 20% to about 31% w/w *Rhizobia* inoculant, preferably about 30% w/w;
from about 0.5% to about 3.0% w/w polyethylene glycol, preferably about 1% w/w polyethylene glycol 200;
from about 0.05% to about 0.5% w/w polysorbate, preferably about 0.1% w/w polyoxyethylene (20) sorbitan monolaurate;
from about 0.3% to about 1.0% w/w silicon dioxide powder, preferably about 0.5% w/w; and
from about 64% to about 74% w/w of a granule comprising from about 47% to about 53% w/w paper fiber, from about 28% to about 34% w/w kaolin clay, from about 14% to about 20% w/w calcium carbonate and titanium oxide.

Preferably the granule is from about 800 to about 1700 microns in diameter.

In a preferred embodiment, the *Rhizobia* inoculant has a *Rhizobia* concentration of about 0.000000001 colony forming units per milliliter.

In another preferred embodiment, the *Rhizobia* granule has a *Rhizobia* concentration of about 0.00000001 colony forming units per gram.

In another embodiment, the present invention is directed to Mycorrhizae granular formulations comprising:
from about 0.01% to about 1.0% w/w Mycorrhizae concentrate, preferably from about 0.06% to about 0.12% w/w;
from about 10% to about 20% w/w soybean oil, preferably about 17.5% w/w;
from about 0.1% to about 0.5% w/w lecithin, preferably about 0.25% w/w;
from about 0.05% to about 0.5% w/w silicon dioxide powder, preferably about 0.1% w/w; and
from about 78% to about 85% w/w of a granule comprising from about 47% to about 53% w/w paper fiber, from about 28% to about 34% w/w kaolin clay, from about 14% to about 20% w/w calcium carbonate and titanium oxide.

Preferably the granule is from about 800 to about 1700 microns in diameter.

In a preferred embodiment, the Mycorrhizae concentrate has a Mycorrhizae concentration from about 200,000 to about 600,000 propagules per gram, preferably 331,200 propagules per gram.

In another embodiment, the present invention is directed to granular mixtures comprising *Rhizobia* granule formulations of the present invention, preferably at a concentration of about 80% to about 90% w/w, more preferably at about 87% w/w and Mycorrhizae formulations of the present invention, preferably at a concentration of about 10% to about 20% w/w, more preferably at about 13% w/w.

In another preferred embodiment, the granular mixtures of the present invention deliver about 90,000 propagules when applied at 4.6 pounds per acre.

In another embodiment, the present invention is directed to granular mixtures comprising *Rhizobia* granule formulations of the present invention and Mycorrhizae formulations of the present invention uniformly blended in a V-cone blender or other suitable blending equipment.

In another embodiment, the present invention is directed to a process for preparing a granular mixture of the present invention comprising:

adding 1 part of the *Rhizobia* granule formulation of the present invention to a V-cone blender;

adding 2 parts of the Mycorrhizae granule formulation of the present invention to the V-cone blender;

adding 1 part of the *Rhizobia* granule formulation of the present invention to the V-cone blender; and blending in the V-cone blender for 5 to 20 minutes.

Compositions of the present invention may be applied to any plant or plant propagation material thereof that may benefit from improved growth including agricultural crops, annual grasses, trees, shrubs, ornamental flowers and the like. Compositions of the present invention may further be applied to any area where a plant will grow including soil, a plant root zone and a furrow.

In another embodiment, the present invention is directed to methods of enhancing plant growth comprising applying a formulation or a mixture of the present invention to the plant, plant propagation material thereof or to any area where a plant will grow.

These representative embodiments are in no way limiting and are described solely to illustrate some aspects of the invention.

The following examples are intended to illustrate the present invention and to teach one of ordinary skill in the art how to make and use the invention. They are not intended to be limiting in any way.

EXAMPLES

Example 1—Preparation of *Rhizobia* Granular Formulations of the Present Invention Tween® 20 is used as the source of polysorbate 20.

Zeofree® 80 (Zeofree is a registered trademark of J.M. Huber Corporation). Zeofree® 80 is used as the source of the silicon dioxide powder and has the CAS no. 112926-00-8.

Biodac® 12/20 Mesh is available from Kadant GranTek Inc. and has the general formula 47% to 53% w/w paper fiber, 28% to 34% w/w kaolin clay, 14% to 20% w/w calcium carbonate and titanium oxide.

TABLE 1

| Rhizobia Granular Formulation | |
|---|---|
| Formulation | R1 |
| Rhizobia Inoculant ($1 \times 10^9$ CFU/mL) | 30.30% |
| Polyethylene Glycol 200 | 1.0% |
| Polysorbate 20 | 0.1% |
| Silicon Dioxide Powder | 0.5% |
| Biodac ® 12/20 Mesh | 68.1% |

Biodac® granules of a 12/20 Mesh (or other suitable grades such as 8/16 Mesh or 20/50 Mesh) are charged to a blender such as Munson blender or cement mixer. PEG-200 and polysorbate 20 are mixed together and added to the *Rhizobia* inoculant to create an inoculant mixture. The inoculant mixture is then sprayed at a controlled rate onto Biodac® granules while blending. Spraying is done intermittently with continuous blending to ensure that the granules are absorbing the inoculant. Silicon dioxide powder is added in one to three steps with intermittent blending. The granules are then packaged into plastic lined high-density polyethylene ("HDPE") pails and stored at 5° C. *Rhizobia* granules are stable.

Example 2—Preparation of Mycorrhizae Granular Formulations of the Present Invention

TABLE 2

| Mycorrhizae Granular Formulation | | |
|---|---|---|
| Formulation | M1 | M2 |
| Mycorrhizae Concentrate (331,200 ppg/g) | 0.12% | 0.06% |
| Soybean Oil | 17.5% | 17.5% |
| Lecithin | 0.25% | 0.25% |
| Silicon Dioxide Powder | 0.1% | 0.1% |
| Biodac ® 12/20 Mesh | 82.03% | 82.09% |

Biodac® granules of a 12/20 Mesh or other suitable grades such 8/16 Mesh or 20/50 Mesh are charged to a blender such as Munson blender or cement mixer. Soybean oil and lecithin are mixed together and the Mycorrhizae concentrate is added to them to create a Mycorrhizae mixture. The Mycorrhizae mixture is then sprayed at a controlled rate onto Biodac® granules while blending. Spraying is done intermittently with continuous blending to ensure that the granules are absorbing the inoculant. Silicon dioxide powder is added in one to three steps with intermittent blending. The granules are then packaged into plastic lined high-density polyethylene ("HDPE") pails and stored at room temperature. Mycorrhizae granules are stable.

Example 3—Preparation of a Homogenous Mixture of *Rhizobia* Granular Formulations and Mycorrhizae Granular Formulations of the Present Invention

TABLE 3

| Mixtures of Rhizobia and Mycorrhizae Granular Formulations | | |
|---|---|---|
| Formulation | GM1 | GM2 |
| R1 | 86.97% | 86.97% |
| M1 | 13.03% | — |
| M2 | — | 13.03% |

1 part of the *Rhizobia* granule formulation R1 is charged to a V-cone blender. 2 parts of the Mycorrhizae granule formulation M1 or M2 is added to V-cone blender. 1 part of the R1 is then added to the V-cone blender and blended for 5 minutes. The resulting granules are a homogenous mixture of R1 and M1 or M2 granules.

What is claimed is:

1. A *Rhizobia* granular formulation comprising:
from about 20% to about 31% w/w *Rhizobia* inoculant;
from about 0.5% to about 3.0% w/w polyethylene glycol;
from about 0.05% to about 0.5% w/w polysorbate;

from about 0.3% to about 1.0% w/w silicon dioxide powder; and from about 64% to about 74% w/w of a granule comprising from about 47% to about 53% w/w paper fiber, from about 28% to about 34% w/w kaolin clay, from about 14% to about 20% w/w calcium carbonate and titanium oxide, wherein w/w denotes weight by total weight of the formulation.

2. The formulation of claim 1, wherein;

*Rhizobia* inoculant is at a concentration of about 30% w/w;

the polyethylene glycol is polyethylene glycol 200 at a concentration of about 1% w/w;

the polysorbate is polyoxyethylene (20) sorbitan monolaurate at a concentration of about 0.1% w/w;

silicon dioxide powder is at a concentration of about 0.5% w/w; and the granule is from about 800 microns to about 1700 microns in diameter.

3. The formulation of claim 1, wherein the *Rhizobia* inoculant has a *Rhizobia* concentration of about 0.000000001 colony forming units per milliliter.

4. The formulation of claim 1, wherein the *Rhizobia* granular formulation has a *Rhizobia* concentration of about 0.00000001 colony forming units per gram.

5. A method of enhancing plant growth comprising applying the formulation of claim 1 to the plant, plant propagation material thereof or to any area where the plant will grow.

6. A Mycorrhizae granular formulation comprising:

from about 0.01% to about 1.0% w/w Mycorrhizae concentrate;

from about 10% to about 20% w/w soybean oil;

from about 0.1% to about 0.5% w/w lecithin;

from about 0.05% to about 0.5% w/w silicon dioxide powder; and from about 78% to about 85% w/w of a granule comprising from about 47% to about 53% w/w paper fiber, from about 28% to about 34% w/w kaolin clay, from about 14% to about 20% w/w calcium carbonate and titanium oxide, wherein w/w denotes weight by total weight of the formulation.

7. The formulation of claim 6, wherein:

Mycorrhizae concentrate is at a concentration from about 0.06% to about 0.12% w/w;

soybean oil is at a concentration of about 17.5% w/w;

lecithin is at a concentration of about 0.25% w/w;

silicon dioxide powder is at a concentration of about 0.1% w/w; and the granule is from about 800 microns to about 1700 microns in diameter.

8. The formulation of claim 6, wherein the Mycorrhizae concentrate has a Mycorrhizae concentration of 331,200 propagules per gram.

9. A method of enhancing plant growth comprising applying the formulation of claim 6 to the plant, plant propagation material thereof or to any area where the plant will grow.

10. A granular mixture comprising the *Rhizobia* granule formulation of claim 1 and the Mycorrhizae formulation of claim 6.

11. The granular mixture of claim 10, wherein the *Rhizobia* granule formulation of claim 1 is at a concentration from about 80% to about 90% w/w and the Mycorrhizae granule formulation of claim 3 is at a concentration from about 10% to about 20% w/w.

12. The granular mixture of claim 10, wherein the *Rhizobia* granule formulation of claim 1 is at a concentration of about 87% w/w and the Mycorrhizae granule formulation of claim 6 is at a concentration of about 13% w/w.

13. The granular mixture of claim 10, wherein the *Rhizobia* granule formulation of claim 1 and the Mycorrhizae formulation of claim 6 are mixed in a V-cone blender.

14. A process for preparing the granular mixture of claim 10 comprising:

adding 1 part of the *Rhizobia* granule formulation of claim 1 to a V-cone blender;

adding 2 parts of the Mycorrhizae granule formulation of claim 6 to the V-cone blender;

adding 1 part of the *Rhizobia* granule formulation of claim 1 to the V-cone blender; and running the V-cone blender for 5 to 20 minutes.

15. A method of enhancing plant growth comprising applying the mixture of claim 10 to the plant, plant propagation material thereof or to any area where the plant will grow.

* * * * *